United States Patent [19]

Hedin et al.

[11] Patent Number: 4,632,829
[45] Date of Patent: Dec. 30, 1986

[54] SEX PHEROMONE COMPOSITION FOR SOUTHWESTERN CORN BORER

[75] Inventors: Paul A. Hedin; Frank M. Davis; Joseph C. Dickens; Marcus L. Burks; Thomas G. Bird, all of Starkville, Miss.

[73] Assignee: The United States of America as represented by the Secretary of Agriculture, Washington, D.C.

[21] Appl. No.: 785,639

[22] Filed: Oct. 8, 1985

[51] Int. Cl.$^4$ ..................... A01N 35/00; A01N 25/00
[52] U.S. Cl. ........................................ 424/84; 514/703
[58] Field of Search ........................... 424/84; 514/703

[56] References Cited

U.S. PATENT DOCUMENTS

| | | |
|---|---|---|
| 3,952,093 | 4/1976 | Roelofs et al. ............. 424/84 |
| 4,216,202 | 8/1980 | Klun et al. ................. 424/84 |
| 4,219,542 | 8/1980 | Klun et al. ................. 424/84 |

FOREIGN PATENT DOCUMENTS 59-184103  10/1984  Japan ................................. 514/703

OTHER PUBLICATIONS

Chem. Abst. 84:87013n (1976)—Nesbitt et al.
Chem. Abst. 88:147450x (1978)—Tatsuki et al.
Chem. Abst. 89:101912s (1978)—Fukunaga et al.
Chem. Abst. 91:51061g (1979)—Tatsuki et al.
Chem. Abst. 93:39436(s) (1980)—Kehat et al.
Chem. Abst. 94:151,842(e) (1981)—Kanno et al.
Chem. Abst. 95:110139(w) (1981)—Bjostad et al.
Chem. Abst. 96:195,065(n) (1982)—Lee et al.
Abst. #44–172nd ACS National Meeting—San Francisco, Ca. Aug. 30–Sep. 3, 1976–Divis. of Pest. Chem.
Abst. #49–186 ACS National Meeting—Washington, D.C. Aug. 28–Sep. 2, 1983–Div. of Pest Chem.
Abstracts—Southwestern Branch Entomiol Soc. Amer., Feb. 21-23, 1983—Corpus Christi, Texas.
News—U.S. Dept. Agri., Apr. 13, 1983—"Identification of Pheromones for Control of Southwestern Corn Borer".

*Primary Examiner*—Douglas W. Robinson
*Attorney, Agent, or Firm*—M. Howard Silverstein; David G. McConnell

[57] ABSTRACT

A sex pheromone composition for southwestern corn borer male moths consisting essentially of Z9-Hexadecenal in an amount of about 16–26% by weight, Z11-Hexadecenal in an amount of about 56–85% by weight, and Z13-Octadecenal in an amount of about 6–10% by weight.

6 Claims, No Drawings

SEX PHEROMONE COMPOSITION FOR SOUTHWESTERN CORN BORER

FIELD

This invention relates to a novel sex pheromone for the male southwestern corn borer moth (SWCB), *Diatraea grandiosella* (Dyar).

PRIOR ART

Many lepidopterous insect pests infest corn, cotton, tobacco and other crops and their larvae cause considerable economic loss. Chemical pesticides have been used to control these insects for many years, but the use of conventional chemicals presents hazards both to man and to the environment. Insecticidal controls have frequently resulted in the development of resistant insect populations.

Females of many lepidopteran species attract males by emitting a sex attractant pheromone. Synthetic sex pheromones have been developed for some of these species which have been used as a lure in insect traps to attract and catch male moths. Such traps have been situated in areas where infestations of the insects normally occur to enable early detection of the moths. Following early detection, other control measures, such as insecticides or release of egg parasites have been employed.

A further application of insect sex pheromones or attractants is their use to suppress insect populations in infested areas by interfering with mating communication. If the air throughout the infested area is permeated with false pheromone signals caused by the dispersal of synthetic pheromones in the infested area, substantial mating disruption may occur resulting in a reduction in future insect population numbers.

The southwestern corn borer (SWCB) is a major pest of corn in parts of the United States. To date, sixteen compounds have been identified in the naturally-occurring sex pheromone produced by SWCB female moths. At first several of these components were thought to be the active ingredients. Subsequently, two of these compounds, Z9-Hexadecenal and Z11-Hexadecenal, in combination with one another, were thought to be primarily responsible as the sex lure.

SUMMARY

We have now discovered that a third component, Z13-Octadecenal, also found in the naturally-occurring pheromone, must be present with the above-mentioned two components in order to elicit a response the same as or greater than that provided by virgin SWCB female moths.

Therefore, it is an object of the present invention to provide an attractant for adult male SWCB moths which will allow effective detection and monitoring of the adult population.

Another object is to provide an attractant which may allow for studies of mating disruption.

Still another object is to provide a novel pheromone for capturing or disrupting the mating activities of SWCB moths.

A further object is to provide a research tool for studying the movement of adult SWCB moths.

Other objects and advantages will be evident from the following more detailed description of the invention.

DETAILED DESCRIPTION

The composition of the present invention consists essentially of Z9-Hexadecenal, Z11-Hexadecenal and Z13-Octadecenal. On a weight basis, the Z9 component is present in an amount of about 17–26%, preferably about 21.5%; the Z11 component is present in an amount of about 56–85%, preferably about 70.6%; and the Z13 component is present in an amount of about 6–10%, preferably about 7.9%. The preferred amounts of the components, expressed on a weight ratio basis, is the same as the weight ratio of these components in the naturally-occurring pheromone for SWCB.

While other compounds found in the naturally-occurring pheromone may be present, these other compounds do not enhance, and in many instance detract from the effectiveness of the composition.

Each individual component is commercially available in substantially pure form, e. g., 99% pure.

In order to apply an effective amount of the composition for the purpose of eliciting a behavorial response in SWCB adult male moths, the composition may be incorporated as part of a pheromone dispenser. As used herein, the term dispenser refers to a substrate such as a membrane, flake, hollow fiber, microcapsule or the like. All these substrates previously have been employed to combat insect pests with sex pheromones.

Rubber or plastic membranes ordinarily are attached to traps as a lure. Typical membrane dimensions are ½" by ¼". Each membrane may contain about 250–3000 micrograms of the composition. A carrier such as hexane may be employed to apply the pheromone to the membrane.

Hollow fibers, flakes and microcapsules may be impregnated with the composition in the prior art manner. Typical carriers for applying the composition to such substrates include hexane, isoctane and methylene chloride. As is known in the art, such flakes, hollow fibers and microcapsules are used to distribute pheromone throughout an area infested with the insect pests, thereby emitting false signals in all directions to cause confusion to the male target population.

As previously mentioned, prior to the present invention, it was believed that only the Z9 and Z11 components in the composition, in combination with one another, were necessary as the attractant. However, field tests showed that, while traps bated with live females attracted 82 males during a 2-week period, a comparable number of traps baited with synthetic formulations containing the Z9 and Z11, without the Z13 component, captured only 5 males. On the other hand, the composition of the present invention has been shown to be as good as and in some tests has substantially outperformed traps having virgin female SWCB moths therein.

We claim:

1. A method of attracting southwestern corn borer male moths to a trap comprising employing as a lure on said trap a sex pheromone composition consisting essentially of Z9-Hexadecenal in an amount of about 16–26% by weight, Z11-Hexadecenal in an amount of about 56–85% by weight, and Z13-Octadecenal in an amount of about 6–10% by weight.

2. The method of claim 1 wherein said Z9-Hexadecenal is present in an amount of about 21.5%, said Z11-Hexadecenal is present in an amount of about 70.6%, and said Z13-Octadecenal is present in an amount of about 7.9%.

3. A method of disrupting the mating activities of southwestern corn borer moths comprising dispersing a synthetic pheromone composition into an area infested with said moths to permeate air throughout said area with false pheromone signals, said composition consisting essentially of Z9-Hexadecenal in an amount of about 16–26% by weight, Z11-Hexadecenal in an amount of about 56–86% by weight, and Z13-Octadecenal in an amount of about 6–10% by weight.

4. The method of claim 3 wherein said Z9-Hexadecenal is present in an amount of about 21.5%, said Z11-Hexadecenal is present in an amount of about 70.6%, and said Z13-Octadecenal is present in an amount of about 7.9%.

5. A sex pheromone composition for southwestern corn borer male moths consisting essentially of Z9-Hexadecenal in an amount of about 21.5% by weight, Z11-Hexadecenal in an amount of about 70.6% by weight, and Z13-Octadecenal in an amount of about 7.9% by weight.

6. A pheromone dispenser for southwestern corn borer male moths, said dispenser impregnated with a sex pheromone composition consisting essentially of Z9-Hexadecenal in an amount of about 21.5%, by weight, Z11-Hexadecenal in an amount of about 70.6% by weight, and Z13-Octadecenal in an amount of about 7.9% by weight.

* * * * *